(12) United States Patent
Grubbs et al.

(10) Patent No.: US 10,357,565 B2
(45) Date of Patent: Jul. 23, 2019

(54) TARGETING MICROBUBBLES

(71) Applicants: California Institute of Technology, Pasadena, CA (US); The Regents of the University of California, Oakland, CA (US)

(72) Inventors: Robert H. Grubbs, South Pasadena, CA (US); Marshall L. Stoller, San Francisco, CA (US); Hoyong Chung, Tallahassee, FL (US); Alissa M. Fitzgerald, San Francisco, CA (US); Thomas W. Kenny, San Francisco, CA (US); Renee M. Thomas, Gainesville, FL (US)

(73) Assignees: California Institute of Technology, Pasadena, CA (US); The Regents of the University of California, Oakland, CA (US)

(*) Notice: Subject to any disclaimer, the term of this patent is extended or adjusted under 35 U.S.C. 154(b) by 0 days.

(21) Appl. No.: 16/154,677

(22) Filed: Oct. 8, 2018

(65) Prior Publication Data
US 2019/0038749 A1  Feb. 7, 2019

Related U.S. Application Data

(62) Division of application No. 15/199,710, filed on Jun. 30, 2016, now Pat. No. 10,149,906, which is a division of application No. 13/593,747, filed on Aug. 24, 2012, now abandoned.

(60) Provisional application No. 61/527,031, filed on Aug. 24, 2011.

(51) Int. Cl.
| | |
|---|---|
| *A61K 41/00* | (2006.01) |
| *A61B 17/22* | (2006.01) |
| *A61K 47/24* | (2006.01) |
| *A61K 31/663* | (2006.01) |
| *A61K 9/00* | (2006.01) |
| *A61K 9/107* | (2006.01) |
| *A61N 7/00* | (2006.01) |
| *A61K 47/69* | (2017.01) |

(52) U.S. Cl.
CPC ...... *A61K 41/0028* (2013.01); *A61B 17/2202* (2013.01); *A61B 17/22004* (2013.01); *A61B 17/22022* (2013.01); *A61K 9/0009* (2013.01); *A61K 9/0019* (2013.01); *A61K 9/1075* (2013.01); *A61K 31/663* (2013.01); *A61K 41/0033* (2013.01); *A61K 47/24* (2013.01); *A61K 47/6911* (2017.08); *A61N 7/00* (2013.01); *A61B 2017/22007* (2013.01); *A61B 2017/22008* (2013.01); *A61N 2007/0039* (2013.01)

(58) Field of Classification Search
CPC ............ A61K 41/0033; A61K 41/0028; A61K 9/0009; A61K 9/1075; A61K 9/0019; A61K 31/663; A61K 47/24; A61K 47/6911; A61B 17/2202; A61B 17/22004; A61N 7/00

See application file for complete search history.

(56) References Cited

U.S. PATENT DOCUMENTS

| | | | |
|---|---|---|---|
| 6,245,318 B1 * | 6/2001 | Klibanov | A61K 49/223 424/9.51 |
| 6,261,537 B1 | 7/2001 | Klaveness et al. | |
| 2007/0110674 A1 | 5/2007 | Xu et al. | |
| 2007/0207194 A1 | 9/2007 | Grayburn et al. | |
| 2008/0045865 A1 | 2/2008 | Kislev | |
| 2008/0269668 A1 | 10/2008 | Keenan et al. | |
| 2009/0136594 A1 | 5/2009 | McLeroy et al. | |
| 2009/0215729 A1 | 8/2009 | Johnson et al. | |

FOREIGN PATENT DOCUMENTS

| | | |
|---|---|---|
| WO | WO 2008/131217 A1 | 10/2008 |
| WO | WO 2012/094541 A2 | 7/2012 |
| WO | WO 2012/143739 A1 | 10/2012 |

OTHER PUBLICATIONS

European Examination Report, European Application No. 12826476.9, dated May 18, 2017, 7 pages.
Rapoport, N. et al., "Multifunctional Nanoparticles for Combining Ultrasonic Tumor Imaging and Targeted Chemotherapy," Journal Natl. Cancer. Inst. Jul. 18, 2007, pp. 1095-1106, vol. 99, Issue 14.
Bhadane, S., "High Intensity Focused Ultrasound and Microbubble Induced Tissue Ablation: Effect of Treatment Parameters on Thermal Lesion Volume and Temperature," Thesis, Ryerson University, 2009, 104 pages.
Bhushan, K. R., et al., "Synthesis of Conjugatable Bisphosphonates for Molecular Imaging of Large Animals," Angewandte Chemie International Edition, 2007, pp. 7679-7971, vol. 46.
Deelman, L. E., et al., "Targeted renal therapies through microbubbles and ultrasound," Advanced Drug Delivery Reviews, 2010, pp. 1369-1377, vol. 62.
Geers, B., et al., "Adeno-associated virus loaded microbubbles as a tool for targeted gene Delivery," Journal of Controlled Release, 2010, 148, e57-e73, p. e59 (abstract).
Hernot, S., et al., "Microbubbles in Ultrasound-triggered drug and gene delivery," Advanced Drug Delivery Reviews, 2008, pp. 1153-1166, vol. 60.
Hu, Y., et al., "Mesenchymal stem cells: A promising targeted-delivery vehicle in cancer gene Therapy," Journal of Controlled Release, 2010, pp. 154-162, vol. 147.

(Continued)

*Primary Examiner* — Johann R Richter
*Assistant Examiner* — Genevieve S Alley
(74) *Attorney, Agent, or Firm* — Fenwick & West LLP

(57) ABSTRACT

This invention related to manufactured microbubbles, as well as methods of using manufactured microbubbles, for example, in medicinal applications. The invention pertains to the physical structure and materials of the microbubbles, as well as to methods for manufacturing microbubbles, methods for targeting microbubbles for specific medicinal applications, and methods for delivering microbubbles in medical treatment.

7 Claims, 5 Drawing Sheets

(56) References Cited

OTHER PUBLICATIONS

Liu, Y., et al., "Encapsulated ultrasound microbubbles: Therapeutic application in drug/gene Delivery," Journal of Controlled Release, 2006, pp. 89-99, vol. 114.
Matheson Tri-Gas, Inc., "Material Safety Data Sheet, Substance: Perfluoropropane," 1989, [online] [Retrieved on Sep. 22, 2016] Retrieved from the Internet <URL: https://www.mathesongas.com/pdfs/msds/MAT18290.pdf>.
Mayer, C. R., et al., "Ultrasonic gene and drug delivery to the cardiovascular system," Advanced Drug Delivery Reviews, 2008, pp. 1177-1192, vol. 60.
Mcdonald, C. J., et al., "Hollow latex particles: synthesis and applications," Advanced in Colloid and Interface Science, 2002, pp. 181-213, vol. 99.
Ramaswamy, K. et al., "Targeted Microbubbles: A Novel Application for the Treatment of Kidney Stones," BJU International, 2015, John Wiley & Sons Ltd., pp. 9-16, vol. 116.
Sirsi, S. et al., "Microbubble Compositions, Properties and Biomedical Applications," Bubble Sci. Eng. Technol., Nov. 2009, pp. 3-17, vol. 1, No. 1-2.
Tinkov, S., et al., "New doxorubicin-loaded phospholipid microbubbles for targeted tumor therapy: Part I—Formulation development and in-vitro characterization," Journal of Controlled Release, 2010, pp. 143-150, vol. 143.
Unger, E. C., et al., "Therapeutic applications of lipid-coated microbubbles," Advanced Drug Delivery Reviews, 2004, pp. 1291-1314, vol. 56.
Wu, T.Y. et al., "Advances in Ultrasound Technology for Environmental Remediation," SpringerBriefs in Green Chemistry for Sustainability, 2013, pp. 5-12.
Yoshizawa, S. et al., "High Intensity Focused Ultrasound Lithotripsy with Cavitating Microbubbles," Med. Biol. Eng. Comput., 2009, pp. 851-860, vol. 47.
PCT Invitation to Pay Additional Search Fees, International Application No. PCT/US2012/052187, dated Nov. 8, 2012, 2 Pages.
PCT International Search Report and Written Opinion, International Application No. PCT/US2012/052187, dated Jan. 28, 2013, 11 Pages.
European Patent Office, Supplementary European Search Report, European Patent Application No. 12826476.9, dated Mar. 11, 2015, 8 Pages.
European Patent Office, Examination Report, European Patent Application No. 12826476.9, dated May 11, 2016, 7 Pages.
United States Office Action, U.S. Appl. No. 13/593,747, dated Oct. 1, 2015, 15 pages.
United States Office Action, U.S. Appl. No. 13/593,747, dated Feb. 13, 2015, 15 pages.
United States Advisory Action, U.S. Appl. No. 13/593,747, dated Mar. 3, 2016, 3 pages.
United States Advisory Action, U.S. Appl. No. 15/199,710, dated Jun. 8, 2017, 4 pages.
United States Office Action, U.S. Appl. No. 15/199,710, dated Jul. 27, 2017, 16 pages.
United States Office Action, U.S. Appl. No. 15/199,710, dated Mar. 13, 2017, 14 pages.
United States Office Action, U.S. Appl. No. 15/199,710, dated Nov. 17, 2016, 11 pages.
Korean Intellectual Property Office, Notification of Reasons for Refusal, KR Patent Application No. 10-2014-7007740, dated Apr. 4, 2019, eight pages.
Unger, E. C. et al., "Therapeutic applications of microbubbles," European Journal of Radiology, vol. 42, Iss. 2, May 2002, pp. 160-168.

\* cited by examiner

TARGETING MICROBUBBLES

CROSS REFERENCE TO RELATED APPLICATIONS

This application is a divisional of U.S. patent application Ser. No. 15/199,710, filed Jun. 30, 2016, which is a divisional of U.S. patent application Ser. No. 13/593,747, filed Aug. 24, 2012, which claims the benefit of U.S. Provisional Patent Application Ser. No. 61/527,031, filed Aug. 24, 2011, each of which is hereby incorporated by reference in its entirety.

FIELD OF THE INVENTION

These inventions are directed toward compositions comprising a bubble forming material, wherein the bubble-forming material comprises an anchoring moiety and a targeting moiety having an affinity for metal-containing, especially calcium-containing, bodies and/or biological targets. In certain embodiments, these compositions are useful for providing targeted placement of microbubbles capable of cavitation on application of high frequency energy.

BACKGROUND OF THE RELATED ART

Cavitation is a component of some currently used medical interventions, such as a treatment for kidney stones. For example, in extracorporeal shock wave lithotripsy, shock waves are focused onto a stone in the kidney or ureter. The interaction between the waves and the stone induces the formation of cavitation bubbles. The collapse of cavitation bubbles releases energy at the stone, and the energy fragments the stone into pieces small enough to be passed via the ureter.

A large number of medical conditions are characterized at least in part by the presence of an abnormal mass. Examples include urinary stones, biliary stones, blood clots, fibroids, cancerous tumors, and atheromatous plaques. Destruction or reduction of the mass without injury to healthy tissue is a goal for many therapeutic treatments. Minimally invasive treatments are preferred as they reduce the pain, discomfort, and risks associated with surgical or other invasive therapies.

SUMMARY OF THE INVENTION

In one aspect, the disclosure provides a target microbubble comprising: (a) a core containing a fluid having a normal boiling point less than about 30° C.; (b) an anchoring moiety comprising a bio-lipid, protein, surfactant, synthetic polymer, or combination thereof; and (c) a targeting moiety comprising a chemical group having an affinity for a metal-containing material, especially calcium-containing, materials, or a small molecule cell specific ligand, including a small molecule tumor cell specific ligand.

In other aspects, certain embodiments provide solutions comprising a plurality of the targeting microbubbles dispersed in a solvent, where the solvent may be water or a physiological fluid.

In another aspect, the disclosure provides methods for preparing a solution, each method comprising combining a bubble-forming material and a solvent, wherein the bubble-forming material comprises an anchoring moiety and a targeting moiety comprising a chemical group having an affinity for a metal-containing material, especially a calcium-containing, material, or a small molecule cell specific ligand, including a small molecule tumor cell specific ligand.

In yet another aspect, the disclosure provides methods for preparing a solution of microbubbles, each method comprising delivering energy to a solution comprising a bubble-forming material and a solvent, wherein: (a) the bubble-forming material comprises an anchoring moiety and a targeting moiety, said targeting moiety comprising a chemical group having an affinity for metal-containing materials, especially calcium-containing, materials or a small molecule cell specific ligand, especially a small molecule tumor cell specific ligand; and (b) the energy is sufficient to cause the bubble-forming material to form microbubbles in the solvent In another aspect, the disclosure provides methods for treating a patient, each method comprising applying energy to microbubbles disposed within the patient, wherein the microbubbles comprise a targeting moiety with a specific affinity to a target within the patient, and wherein the energy is effective to cause cavitation of the microbubbles. In another aspect, the disclosure provides a method for treating a patient, the method comprising: (a) delivering a solution comprising microbubbles to a site within the patient; and (b) applying energy to the microbubbles, wherein the energy is in the form of electromagnetic, ultrasound, microwave, or other energies and is sufficient to cause cavitation of the microbubbles, and wherein the cavitation releases sufficient energy to cause destruction of a cell, tissue, or calculous mass at the site within the patient.

These and other aspects will be apparent from the disclosure provided herein, including the claims, figures, and examples.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 4A illustrates the successful attachment of the microbubble to the kidney stone (calculous). Without the pretreatment described in Example 5, the microbubbles did not attach. FIG. 4B shows an in situ picture of the microbubble bursting. FIG. 4C shows the multiple pitting damage caused by the cavitation. The surface of this stone was smooth before microbubble treatment.

DETAILED DESCRIPTION OF THE PREFERRED EMBODIMENTS

Figure 1:
FIG. 1 provides a photographic image of a kidney stone after an in vivo treatment using a method according to the disclosure.

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Additionally, throughout this text, it is recognized that the descriptions refer both to the compositions comprising and methods of making and using targeting microbubbles. These certain compositions or methods may be described in terms of certain embodiments or features. Where the disclosure describes and/or claims a particular feature in a composition or method, it is appreciated that such a feature is intended to relate to all compositions or methods described herein.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

As used herein the term "microbubble" refers to any container, coil, or other space conforming geometry. Unless otherwise specified, the terms "microbubbles" and "bubbles" are used interchangeably.

Definitions of other terms and concepts appear throughout the detailed description below.

In some aspects of the disclosure, there is herein provided methods and materials for synthesizing microbubbles for medical applications. Chemical tags are attached to biocompatible microbubbles and the microbubbles are then delivered to a patient. The chemical tags have an affinity for a targeted mass, tissue, or structure, such that microbubbles concentrate near the target. Ultrasound or another suitable form of energy is then applied causing the microbubbles to induce cavitation. Cavitation of microbubbles causes the delivery of energy at or near the target. For example, where the target is an unwanted mass, cavitation causes the mass to break apart into smaller pieces that may be removed from the patient or may pass from the patient via normal biological processes. In another example, where the target is a biological entity such as a tissue or cell, cavitation causes destruction of the entity and/or disruption of biological processes involving the entity.

Various embodiments of the present invention provide methods for preparing a solution, each method comprising combining a bubble-forming material and a solvent, wherein the bubble-forming material comprises an anchoring moiety and a targeting moiety a targeting moiety comprising: (i) a chemical group having an affinity for a metal-containing material; or (ii) a cell specific ligand.

Still other embodiments provide targeting microbubbles, each microbubble comprising: (a) a core containing a fluid having a normal boiling point less than about 30° C.; (b) an anchoring moiety comprising a bio-lipid, protein, surfactant, or synthetic polymer; and (c) a targeting moiety comprising: (i) a chemical group having an affinity for a metal-containing material; or (ii) a cell specific ligand. In certain of these embodiments, the targeting moiety may either have an affinity for a metal-containing material; e.g., a calcium-containing material, such as a atheromatous plaque, biliary stone, a calcified tissue or plaque, a cancerous tumor, or a urinary stone; or, by virtue of a small molecule cell specific ligand, have an affinity for blood clots, fibroids, cancerous tumors, and/or atheromatous or other plaques.

Other embodiments provide solutions, each comprising a plurality of targeting microbubbles dispersed in a solvent, wherein the solvent may include water or some other physiological fluid. As used herein, the term "physiological fluid" refers to a fluid of the body, for example, including blood, lymph fluid, saliva, bile, urine, and interstitial fluid.

In these, and other embodiments throughout this disclosure, such calcium-containing materials may be found within or outside the body of a patient, for example, including atheromatous or other calcium-containing plaque (e.g., dental plaque), biliary stone, a calcified tissue or plaque, a cancerous tumor, or a urinary stone. Also, as used herein, the term "targeting moiety having an affinity to metal- or calcium-containing materials" refers to a chemical moiety, which by virtue of its chemical affinity for metal- or calcium salts (e.g., calcium carbonate, calcium oxalate, calcium phosphate, or hydroxyapatite) has a tendency to complex with such salts. Bisphosphonate is one such moiety particularly useful for calcium-containing materials, and is a preferred embodiment of the present invention.

As used herein, the term "small molecule cell specific ligand" is intended to connote a ligand comprising a cell specific ligand having a molecular weight less than about 1000 Daltons and having an affinity for a particular type of cell or cells, and be distinguished from antibody or protein-based ligand. In certain embodiments, the cell specific ligand is a cancer tumor cell specific ligand, such as a folate (see, e.g., Example 6, below), which is known to be a very selective receptor to cancerous tumors and it is not harmful to healthy cells.

In each of the embodiments contemplated herein, the anchoring moiety and the targeting moiety of the various embodiments may be linked by one or more covalent, ionic, or hydrogen-bonding linkages. In such embodiments, the bubble-forming material may further comprise a polymeric linking moiety that covalently links the anchoring moiety with the targeting moiety, as discussed below. In other embodiments, the anchoring moiety is directly chemically attached to the targeting moiety. Further, the anchoring moiety may comprise a bio-lipid, synthetic polymer, surfactant, and/or a protein.

Where the targeting microbubbles comprise a core containing a fluid having a normal boiling point less than about 30° C. or 35° C., such may comprise air, $CO_2$, a fluorinated or perfluorinated $C_{1-6}$ hydrocarbon (e.g., perfluoropropane), or a combination thereof. In some embodiments, the core may comprise a fluid comprising a condensed gas; i.e., the composition is at a temperature below the boiling point of the fluid. For example, pentafluoropentane, with a boiling point of 29.5° C., may exist as a liquid at ambient temperature, but as a gas at physiological temperatures (e.g., 37° C.). Such a fluid is considered within the scope of the present invention.

This invention also teaches methods for preparing a solution of microbubbles, each method comprising delivering energy to a solution comprising a bubble-forming material and a solvent, wherein the bubble-forming material comprises an anchoring moiety and a targeting moiety, such that the energy is sufficient to cause the bubble-forming material to form microbubbles in the solvent. Again, in these embodiments, the targeting moiety also either have an affinity for a calcium-containing material (or other metal target) or, by virtue of a small molecule cell specific ligand, have an affinity for blood clots, fibroids, cancerous tumors, and/or atheromatous or other plaques. In various embodiments, the bubble-forming material further comprises a bio-lipid, surfactant, synthetic polymer, or protein, wherein the compound is not chemically linked to the targeting moiety.

Additional embodiments provide methods of treating a patient, each method comprising applying energy to microbubbles disposed within the patient, wherein the microbubbles comprise a targeting moiety with a specific affinity to a target within the patient, and wherein the energy is effective to cause cavitation of the microbubbles. In certain embodiments, the methods further comprise administering the microbubbles to the patient prior to applying the energy, for example via injection, inhalation, or implantation. In some of these embodiments, the target is a calcium-containing mass, a cancerous cell, a tumor, or a tissue. In some embodiments where the target is a calcium-containing mass, the cavitation causes damage to the target. In other embodiments where the target is a cancerous cell, the cavitation causes lysis of the target. In still other embodiments where the target is a renal or urinary stone, biliary stone, blood clot, fibroid, cancerous tumor, or atheromatous or other plaque, the cavitation causes damage to the target. In certain of these embodiments, the microbubbles further comprise a bio-lipid, synthetic polymer, protein, or surfactant, but the compound is lacking a targeting moiety. The microbubbles may be alternatively attached to the target, or not attached, in the latter case being proximate to the target.

Still other embodiments include methods of treating a patient, each method comprising: (a) delivering a solution comprising microbubbles to a site within the patient; and (b) applying energy to the microbubbles, wherein the energy is in the form of electromagnetic or ultrasound energy and is sufficient to cause cavitation of the microbubbles, and wherein the cavitation releases sufficient energy to cause destruction (e.g., lysis or fracture) of the target cell, tissue, tumor, or calcium-containing or other mass at the site within the patient—e.g., to the target renal or urinary stones, biliary stones, blood clots, fibroids, cancerous tumors, and atheromatous plaques. In certain related embodiments, the microbubbles do not contain a targeting moiety. In these embodiments, the solution may be delivered by any method described herein for such purpose, but especially via implantation, inhalation, injection, or by catheter. Where by inhalation or injection, it is envisioned that the microbubbles have an affinity for a cell, tissue, or calcium-containing mass at that site within the patient.

Various microbubble products are available commercially, including microbubbles marketed under the trade names ALBUNEX®, DEFINITY®, and OPTISON®. In some embodiments, the microbubbles used in the procedures described herein are selected from such commercially available materials and are further modified to include targeting moieties as described herein.

An example for illustrative purposes is provided as follows. In one embodiment, microbubbles are prepared having chemical tags that are suitable for binding to kidney stones. Such chemical tags may be, for example, bisphosphonate pendants. The microbubbles are administered to a patient suffering from kidney stones. Ultrasound is applied to cause the microbubbles to cavitate and break apart the kidney stones into smaller particles. The smaller particles pass through the kidney/ureter naturally and with limited or no discomfort to the patient.

Prior medical applications of cavitation have used extracorporeal energy sources to create and collapse air bubbles in the tissue. The methods disclosed herein differ from such procedures by utilizing application-specific, gas-containing bubbles that are manufactured ex-vivo. The manufactured bubbles are specifically delivered to the surface or vicinity of the targeted tissue or mass. Alternatively, the bubbles contain targeting tags that allow them to concentrate on or near the targeted tissue or mass. Energy from external sources (e.g. ultrasound, RF energy, or the like) is then applied in order to induce cavitation. The engineered bubbles act as a cavitation nucleus upon interaction with ultrasound or by absorption of radio frequency energy causing local heating and cavitation. Expansion of bubbles and their rapid collapse causes a shock wave that can fragment or lyse the targeted mass. For certain masses, the release of energy will cause fragmentation, as in the case of kidney stones. For other conditions, the energy release will cause the lysis of cells, as in tumors.

Microbubble Characteristics

The microbubbles of interest include a shell surrounding a hollow core. In some embodiments, the shell is composed of bio-lipids, proteins (e.g., albumin), surfactants, biocompatible polymers, or any combination thereof. Specific examples of such materials are provided herein below. In some embodiments, the hollow core is filled with a gas or low boiling fluid, and examples of such gases and fluids are also provided herein below. The microbubbles are designed with a shape and size to nucleate cavitation, which refers to the formation and collapse of gaseous bubbles. The violent collapse of cavitation bubbles releases energy that can cause the fragmentation of an adjacent mass.

In some embodiments, the microbubbles described herein are modified to carry chemical tags (referred to herein as "targeting moieties" or "functional moieties") on or near their surface. Such tags are selected to target specific locations, masses, or structures in vivo. Because of the targeting, microbubbles concentrate at the targeted location, mass, or structure and can be used in therapeutic treatments as described herein.

Alternatively or in addition, the microbubbles can be used to transport a load of material within the core to a specific mass, location, or structure in vivo.

For example, gas-filled microbubbles are synthesized with one or more tags for targeting a specific tissue, tumor, mass, stone or bone. The bubbles are delivered to the target as part of a pharmaceutically acceptable formulation. Upon attachment to or association with the target, cavitation is induced with consequent disruption or fragmentation of the target.

The contents of the bubble can vary with application. In some embodiments, the bubble contains air, $CO_2$, a fluorinated or perfluorinated gas (e.g. a perfluorinated alkane such as perfluoropropane), another gas, or mixtures thereof. In other embodiments, the bubble may contain a low boiling (e.g., normal boiling point less than about 30° or 35° C.). This allows that a deflated bubble may be injected into the patient, said bubble inflating as it heats to physiological temperatures (ca. 37° C.). In other embodiments, the bubbles can be filled partially or completely with a payload other than a gas, such as a pharmaceutically active agent, a cytotoxic agent, an imaging agent, or the like.

The bubbles are intended for delivery to the site of a targeted mass or tissue that is to be reduced in size or eliminated. The bubbles are tagged with a targeting moiety so that they selectively bind or associate with the target.

Various sizes and shapes of bubbles are suitable based on the specific intended applications. In some embodiments, the microbubbles are selected from spherical, ellipsoidal, disk-shaped, and asymmetric shapes. In some embodiments, the shape of the bubbles is not static. For example, in some embodiments, the unperturbed bubbles may be spherical, but the bubbles may adopt a different shape such as ellipsoidal or disk-shaped when an external force (e.g., a flowing fluid such as blood) is present.

In some embodiments, the microbubbles have an average diameter (wherein "average diameter" refers to the largest dimension for non-spheroidal shapes) between 0.1 μm and 10 μm, or between 0.5 μm and 10 μm, or between 1 μm and 10 μm. In some embodiments, the average diameter is between 0.5 μm and 3 μm, or between 1 μm and 2 μm. In some embodiments, the microbubbles have an average diameter less than 10 μm, or less than 5 μm, or less than 1 μm, or less than 0.5 μm, or less than 0.1 μm. In some embodiments, the microbubbles have an average diameter greater than 0.1 μm, or greater than 0.5 μm, or greater than 1 μm, or greater than 5 μm, or greater than 10 μm. The synthetic processes described herein allow the production of bubbles of various sizes and materials. It will be appreciated that use of the term "microbubbles" is not intended to limit the size of the bubbles to any particular range (e.g., micron diameters).

In some embodiments, the microbubbles are targeted to the mass of interest by the attachment of a targeting agent or tag, for example to the surface of the bubble. For example, microbubbles can be chemically functionalized using a variety of techniques, the details of such techniques being dependent on the exact chemical moiety to be attached.

Examples of methods of attachment of the targeting moieties include covalent and ionic bonds. The targeting moiety is chosen based on properties of the target tissue or mass as well as the structure and chemical properties of the microbubbles. A variety of targeting moieties may be used, some of which are described in more detail below.

Targeting moieties and other functional groups can be attached asymmetrically or in patterns as needed for a particular application. In some embodiments there is directional modification of the surface of the bubbles. For some applications, only one part of the surface of the microbubble is functionalized with a tagging moiety in order to direct energy toward or away from the intended target.

Delivery and Administration

Delivery into or near the targeted mass, tissue, tumor, stone, bone or other site of interest can be achieved by a variety of means, as appropriate for the application. Bubbles may be introduced, as examples, by injection or spray. Depending on specific formulations, preparations may be prepared using surfactants or other additives for dispersal. In some embodiments, bubbles are introduced to the blood, bile, urine, or cerebral spinal fluid. In some embodiments, bubbles are introduced to organs by percutaneous injection. In some embodiments, bubbles are introduced via an orifice of the body. Orifices include any opening such as the mouth, nose, eyes, vagina, urethra, and ears. In some embodiments, bubbles are introduced under the skin.

In some embodiments, bubbles are introduced directly at the target site, such as by direct implantation into a target tissue or mass. In some such cases, it is not necessary for the bubbles to be manufactured with targeting agents.

In other embodiments, bubbles are introduced at a remote location (e.g., into the bloodstream via percutaneous injection) and are allowed to concentrate at the targeted site.

In each of these methods it will be appreciated that the bubbles are introduced as part of a pharmaceutical formulation which may include, for example, solvents or other carriers, additives (e.g., stabilizers and preservatives, colorants, surfactants, pH-modifiers, etc.), and/or one or more pharmaceutically active agents.

Treatment

After introduction of the bubbles and attachment or association of the bubbles with the target, cavitation may be initiated by a variety of means. In some embodiments such means involve application of energy, where such energy is generated ex vivo. Examples include application of directed ultrasound and radio waves. In some embodiments, electromagnetic (EM) energy of frequencies between 400 kHz and 10 MHz is suitable because it propagates through tissue without strong interactions (due to low electrical conductivity). In one example, standard ultrasound units are applied within or adjacent to the body with sufficient power to initiate cavitation of the pre-positioned bubbles.

Materials and Methods

In some embodiments, preparations of the microbubbles used herein are carried out according to literature procedures, with appropriate modifications as necessary. The functionalized (i.e., tagged) microbubbles may be prepared by functionalizing a bubble-forming material. Alternatively, microbubbles can be prepared from un-functionalized materials and then subsequently functionalized after bubble formation.

In some embodiments, microbubbles suitable for medicinal applications are prepared by adapting a process for creating hollow spheres for use in paints and surface treatments (C. J. McDonald and M. J. Devon, Advanced in Colloid and Interface Science, 2002, 99, 181-213).

In some embodiments, microbubbles (including multilayered microbubbles) are prepared using methods known in the art; for example, according to the process reported in Liu et al., J. Controlled Release, 114 (2006) 89-99, and references cited therein. In some embodiments, microbubbles are prepared according to the process reported in Hu et al., J. Controlled Release, 147 (2010) 154-162, and references cited therein. In some embodiments, microbubbles are prepared according to the process reported in Hernot et al., Adv. Drug Delivery Rev. 60 (2008) 1153-1166, and references cited therein. In some embodiments, microbubbles are prepared according to the process reported in Geers et al., J. Controlled Release 148 (2010) e57-e73 (abstracts), and references cited therein. In some embodiments, microbubbles are prepared according to the process reported in Tinkov et al., J. Controlled Release 143 (2010) 143-150, and reference cited therein. Additional synthetic details for preparing (untagged) microbubbles can be found in Mayer et al., Adv. Drug Delivery Rev. 60 (2008) 1177-1192. The procedures from any of the above-cited references can be modified according to the examples provided herein below so as to prepare the targeting microbubbles of interest.

Various materials can be used in the manufacture of bubbles. In some embodiments, the bubble-forming material includes an anchoring moiety and a targeting moiety. In some embodiments, the anchoring moiety is hydrophobic and the targeting moiety is hydrophilic. Alternatively, the anchoring moiety is hydrophilic and the targeting moiety is hydrophobic. It will be appreciated that in either of these cases, the bubble-forming material is amphiphilic. The bubble-forming material may further contain one or more additional moieties as described below In some embodiments, the various components of the bubble-forming material are chemically bonded to each other via covalent bonds, ionic bonds, hydrogen bonds, or a combination thereof. In some embodiments, two or more of the various components are separate molecules (not chemically bonded) but are associated with each other as part of the same microbubble. For example, the "anchoring moiety" may be a separate compound from the "targeting moiety," and both compounds together form microbubbles.

In some embodiments, the targeting moiety comprises a chemical group having an affinity for a metal-containing material. As used herein, a metal-containing material comprises any of the elements of Group 2 to Group 12, and the metals of Groups 13-15, though materials comprising calcium are especially attractive targets for the present invention. The variety of structured, chemical, and other characteristics capable of providing an affinity to a metal-containing material are too numerous to mention here, but are known to those skilled in the art. For example, such groups will generally include functional groups capable of interacting with such surfaces; e.g., heteroatoms such as nitrogen, oxygen, sulfur and phosphorus. One such chemical group may be a bi- or poly-dentate chelant having at least two amino, carboxy, hydroxyl, phosphoryl, or thiol groups, or a combination thereof. Examples include amino acids or polyamino acids, triols, polyamines, polycarboxylates, or combinations thereof.

In some embodiments, the targeting moiety is a phosphonate such as a bisphosphonate. Bisphosphonates are useful agents for targeting renal or urinary stones, and are part of a family of bone-targeting agents (any of which may be used herein as desired). For example, neridronate and alendronate have the appropriate functionality to attach to kidney stones and other calculous masses. Other targeting moieties include antibodies and specific antigens (e.g. biotin/streptavidin).

In some embodiments, the targeting moiety is a cytokine or chemokine suitable for targeting the microbubbles to cells expressing a corresponding receptor. Examples of suitable ligands are provided in Hu et al., J. Controlled Release, 147 (2010) 154-162. Such ligands may be incorporated into the microbubbles via attachment to a bubble-forming material, or may be used as a bubble-forming material and thereby incorporated directly into the microbubbles. Examples of suitable receptors that can be targeted in this manner are also reported in Hu et al.

In some embodiments, the targeting moiety does not provide targeting per se, but provides one or more functional properties. For example, functionalizing markers include metal complexes, spin labels, and fluorescent tags or radioactive labels to enhance identification with routine radiographic, ultrasound or magnetic resonance imaging. Such functional moieties are particularly suitable where the microbubbles are intended for direct implantation at or near the target. In some embodiments, a combination of functional moieties and targeting moieties are used.

In some embodiments, the anchoring moiety is selected from bio-lipids (e.g. phospholipids), surfactants, proteins (e.g., denatured human serum albumin), or biocompatible synthetic polymers, or combinations thereof.

For example, the anchoring moiety may be a synthetic polymer. Some examples of suitable polymers include PEG, polylactide, polyglycolide polyacrylates, polymethacrylates, and vinyl polymers such as polystyrene, as well as co-polymers thereof (e.g., poly(lactide-co-glycolide)). The structure and molecular weight of the polymer can be adjusted based on the desired application. In some embodiments, the molecular weight of the polymer is less than about 10,000 Da, or less than about 5000 Da, or less than about 1000 Da. In some embodiments, the molecular weight of the polymer is greater than about 1000 Da, or greater than about 5000 Da, or greater than about 10,000 Da. The polymer may be linear or non-linear, such as branched or comb-like.

In some embodiments, the anchoring moiety is a surfactant or phospholipid that further comprises an attached polymeric moiety. In some such embodiments, the polymeric moiety functions as a linker that links the targeting moiety to the anchoring moiety. For example, PEG moieties of various lengths (e.g., 1-30 repeat units as described above) can serve to provide a flexible linker moiety.

Some examples of additional moieties that may be included in the bubble-forming material include lipids and steroids. For example, a cholesterol moiety may be included as described below.

In some embodiments, the targeting moiety is chemically attached to the anchoring moiety. Such chemical attachment includes attachment via a covalent, ionic, or hydrogen bond. In some embodiments, as described previously, a linking moiety is present, and the targeting moiety and anchoring moiety are indirectly chemically attached via the linking moiety.

Chemical attachment (also referred to as conjugation) of the targeting moiety to the anchoring moiety (either directly or via a linking moiety) may be carried out using any of the methods described herein, as well as standard synthetic methods such as via the use of thioether, amide, or disulfide bonding. The conjugation reaction may be carried out prior to or after bubble formation.

In some embodiments, each molecule of bubble-forming material contains a single targeting moiety, whereas in other embodiments each molecule contains a plurality of targeting moieties. For example, a bubble-forming material prepared from a branched polymer may contain numerous targeting moieties (e.g., one targeting moiety at the end of each branch in the polymer).

In some embodiments, the microbubbles are prepared from a single bubble-forming material such as those described above. In such embodiments, each microbubble contains at least as many targeting moieties as individual molecules, because each bubble-forming molecule contains at least one targeting moiety.

In some embodiments, the microbubbles are prepared from a mixture of materials. In some such embodiments, one or more of the bubble-forming materials may be functionalized with a targeting moiety, while one or more of the bubble-forming materials does not contain a targeting moiety. By mixing functionalized with un-functionalized bubble-forming materials in this manner, the density of targeting moieties on each microbubble can be adjusted as desired.

In some embodiments, the targeting moieties are disposed exclusively on the exterior surface of the microbubbles. In other embodiments, some or all of the targeting moieties are disposed beneath the exterior surface of the microbubbles. It will be appreciated that the location of the targeting moieties may be dependent upon environmental conditions such as solvent polarity, pH, ionic strength, etc., and may change with changing conditions.

An alternative method for manufacturing medical bubbles incorporates techniques used in fabrication of titanium micro-electromechanical systems (MEMS). MEMS technology is used to form shaped spheres. The fabrication process uses well established micro-processing techniques.

Suitable methods for storage of the bubbles are determined according to properties and applications of specific bubbles and may require water, surfactant, oil or other medium.

In one particular example, the bubble-forming material is a bisphosphonate having the structure shown below:

In this example, the PEG chain lengths may be varied from 1 to 30 or greater. This material may be synthesized analogously to the procedure outline in Bhushan et al., Angewandte Chemie International Edition 2007, 46, 7969-7971. A similar example is a cholesterol derivative containing a phosphonate moiety with the following structure:

In another specific example, the microbubbles are formed from a lipid shell. Between about 1% and about 25% of the lipid molecules are covalently attached to polymer molecules, with the percentage being selected based on a variety of factors such as polymer molecular weight and the identity of the microbubble components. The polymer molecules form a stabilizing layer around the shell. Some or all of the stabilizing polymer molecules contain an attached targeting moiety that is suitable for the desired application. For example, the material described in Deelman et al., Adv. Drug Delivery Rev. 62 (2010) 1369-1377 can be modified according to the procedures disclosed herein in order to contain appropriate targeting moieties.

As illustrated in the Examples included below, solutions of microbubbles may be prepared by combining the bubble-forming material with a solvent and then applying energy to induce bubble formation. In some embodiments, such energy is applied in the form of mechanical (vibrational) energy by shaking or otherwise mixing the solution. In some embodiments, such energy is applied in the form of ultrasound energy sufficient to induce bubble formation (but not sufficient to induce cavitation). As used herein, the term "pre-bubble solution" refers to a solution comprising a bubble-forming material and a solvent prior to the application of energy sufficient to induce bubble formation. It will be appreciated, however, that a solution of microbubbles may, over time, revert back to the state of the pre-bubble solution (i.e., where bubble-forming material is present but no bubbles are present). It will further be appreciated that the microbubbles can be re-formed by applying additional bubble-forming energy.

Formulation

The manufactured bubbles can be prepared for introduction to a human patient, for example by injection, spray, implantation, or the like. As required for medical applications, bubbles are prepared as effective amounts in a pharmaceutical preparation in a pharmaceutically acceptable carrier.

In some embodiments, the microbubble product is prepared for introduction to a patient or subject. The product may be dispersed in fluid for injection or formulated as an aerosol spray for introduction near the target.

In some embodiments, the microbubbles are prepared as a slurry or emulsion suitable for injection, administration via an aerosol spray, or introduction via a catheter.

In addition to the microbubbles and a pharmaceutically acceptable carrier, various other agents may be added to the formulations as desired. In some embodiments, one or more surfactants are included in the formulation. In other embodiments, no surfactants are added to the microbubble formulation. Other additives that may be present include pH-modifying agents, preservatives, labeling compounds and/or image enhancing compounds, salts, and the like.

Applications

The methods and materials described herein are appropriate for many applications. For example, medicinal bubbles as disclosed herein are suitable to be used in both human and animal medicine as well as in experimental models.

In some embodiments, the methods and materials of interest provide minimally invasive treatment of medical conditions, including treatments that do not require expensive and bulky equipment for administration to a patient.

A large number of medical conditions are characterized at least in part by the presence of an abnormal mass. Examples include urinary stones, biliary stones, blood clots, fibroids, cancerous tumors, and atheromatous plaques. The methods and materials described herein provide destruction or reduction of the mass with minimal injury to healthy tissue and thus provide therapeutic benefit. The therapeutic methods are minimally invasive and are characterized by reduced pain, discomfort, and risks that are associated with open surgical or other invasive therapies.

In a specific example, the methods and materials disclosed herein are suitable for the treatment of kidney stones. In one example of such treatment, targeting microbubbles are injected into the ureter, and upon binding to the kidney stone, ultrasound is applied either locally or via an extracorporeal source to cause cavitation of the microbubbles. This cavitation breaks apart the kidney stone into small particles that can be released by the body, for example following the administration of a diuretic.

The following are additional examples of uses of the materials and methods disclosed herein. Such examples are not intended as a limitation on the invention.

A microbubble solution may be prepared for injection into excess adipose tissue to remodel or destroy intended targets.

A microbubble solution may be prepared for injection into the lens capsule for subsequent removal in cataract surgery.

A microbubble solution may be prepared for injection into joints to destroy offending cartilage or to facilitate remodeling of bone.

A microbubble solution may be prepared for injection into blood stream to target and lyse occlusive blood clots.

A microbubble solution may be prepared for injection into blood streams to target and fracture atheromatous plaques.

A microbubble solution may be prepared for injection into targeted tissue to facilitate fenestration.

A microbubble solution may be prepared for injection into posterior pharynx to induce scarring to alleviate sleep apnea.

A microbubble solution may be prepared for injection into mammary tissue to facilitate breast reductions.

A microbubble solution may be prepared for injection into reproductive tract to facilitate sterilization.

A microbubble solution may be prepared for ex-vivo applications to target selected sperm (male vs. female).

EXAMPLES

Example 1: Synthesis of Targeting Microbubbles

A solution of microbubbles is synthesized according to the following procedure.

First, a modified bisphosphonate lipid is synthesized. The amine group of compound 1, which is commercially available, is protected as shown to give compound 2. The phosphonate hydroxyl of 2 will subsequently be methylated to yield 3, which is reacted with trifluoroacetic acid in methylene chloride to generate product 4.

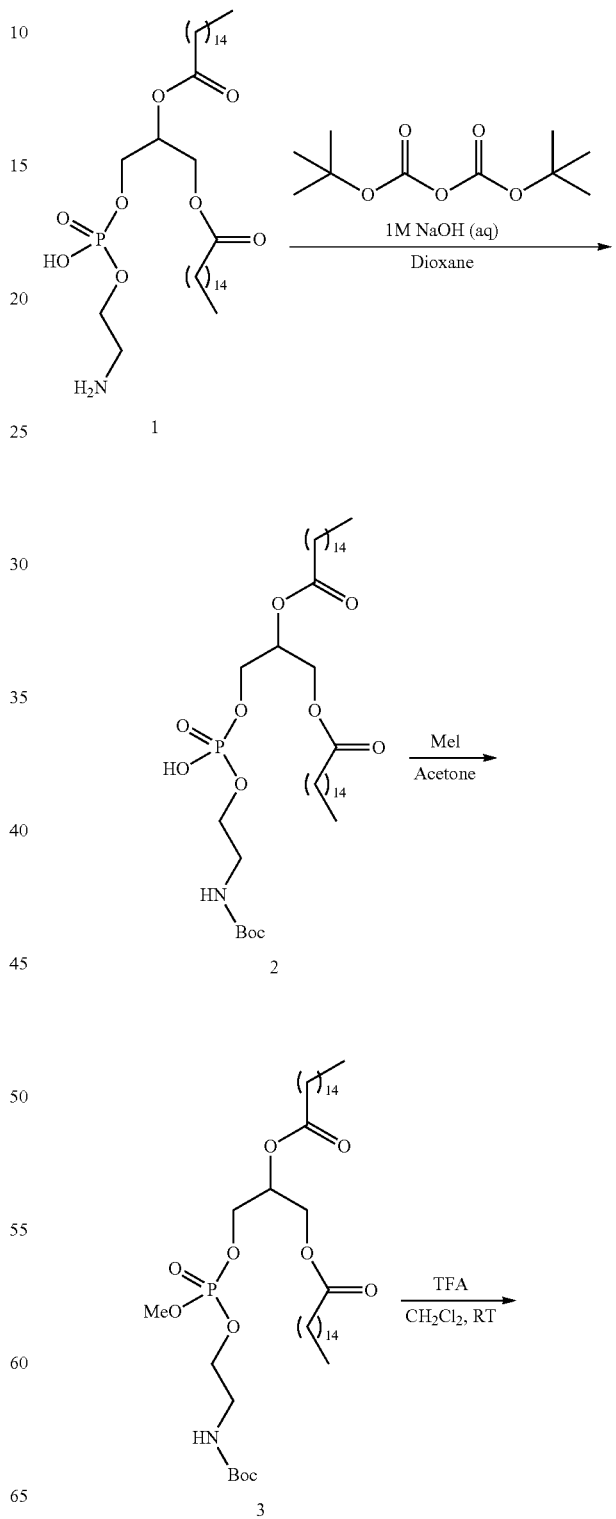

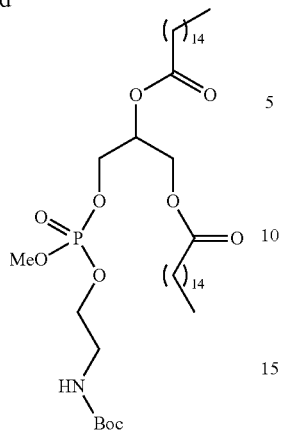

4

Concurrently, compound 5, which is commercially available, is reacted to form 6, which is directly carried on to form compound 7. This procedure is done following a method discussed in Bhushan et al., Angewandte Chemie Chemie Int. Ed. 2007, 46, 7969-7971.

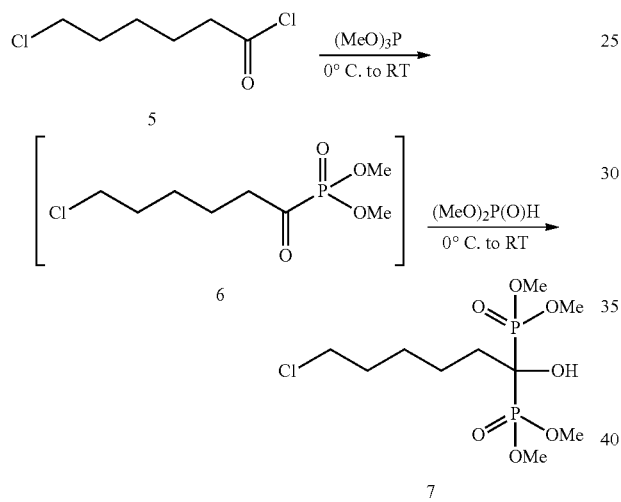

Products 4 and 7 are then coupled together in the presence of base and heat to yield compound 8. Deprotection of the methoxy functionalities to hydroxyl functionalities affords target product 9.

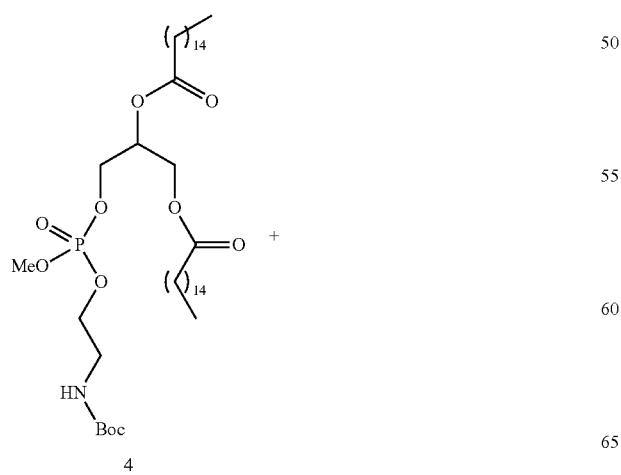

4

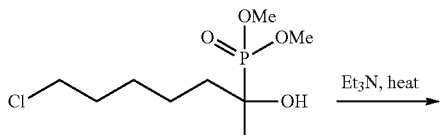

7

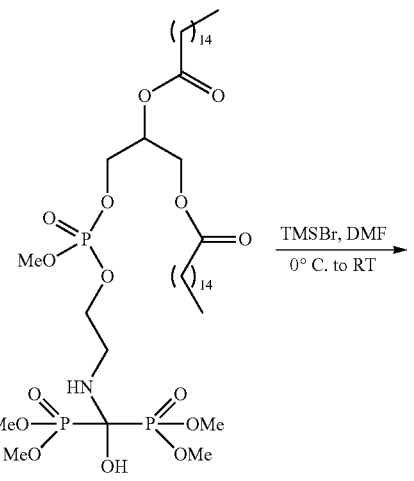

8

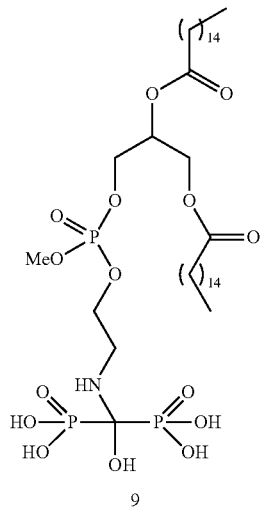

9

The microbubble solution is then prepared as follows. The concentrations and solutions are prepared to mimic "Definity" microbubbles (see Example 2 for general procedure). For a 50 mL solution of the proper concentrations, a buffer solution is made as follows. Propylene glycol (5.1750 g), glycerin (6.3100 g), NaPhosphate monobasic.times.1H2O (0.1170 g), NaPhosphate dibasic 10-hydrate (0.1080 g), and NaCl (0.2435 g) are combined with 25 mL of distilled water, measured with a volumetric flask. The lipid solution is prepared in chloroform. Ten mL stock solutions of each of the lipids are made in chloroform, and a 25 mL solution is made from these stock solutions. For DPPA, 4.5 mg is combined with 10 mL of chloroform in a 10 mL volumetric flask. For lipid 9, 26.67 mg is added with 10 mL of chloroform in a 10 mL volumetric flask, and likewise for MPEG5000 DPPE, 30.4 mg is combined with 10 mL of chloroform in a 10 mL volumetric flask. Subsequently 5 mL of each of the stock solutions is combined, and this combined solution is diluted to a 25 mL volume of chloroform in a 25 mL volumetric flask. This 25 mL lipid solution will then be added with the 25 mL buffer solution to make the final microbubble solution in a total volume of 50 mL. The solution is distributed to vials, and the headspace is filled with octafluoropropane gas through a septum cap. The vials is sealed and stored at a cool temperature. The microbubbles are generated when desired by shaking using a Vialmix shaker or an equivalent shaker.

In an alternative synthesis, targeting microbubble materials are prepared according to the following scheme:

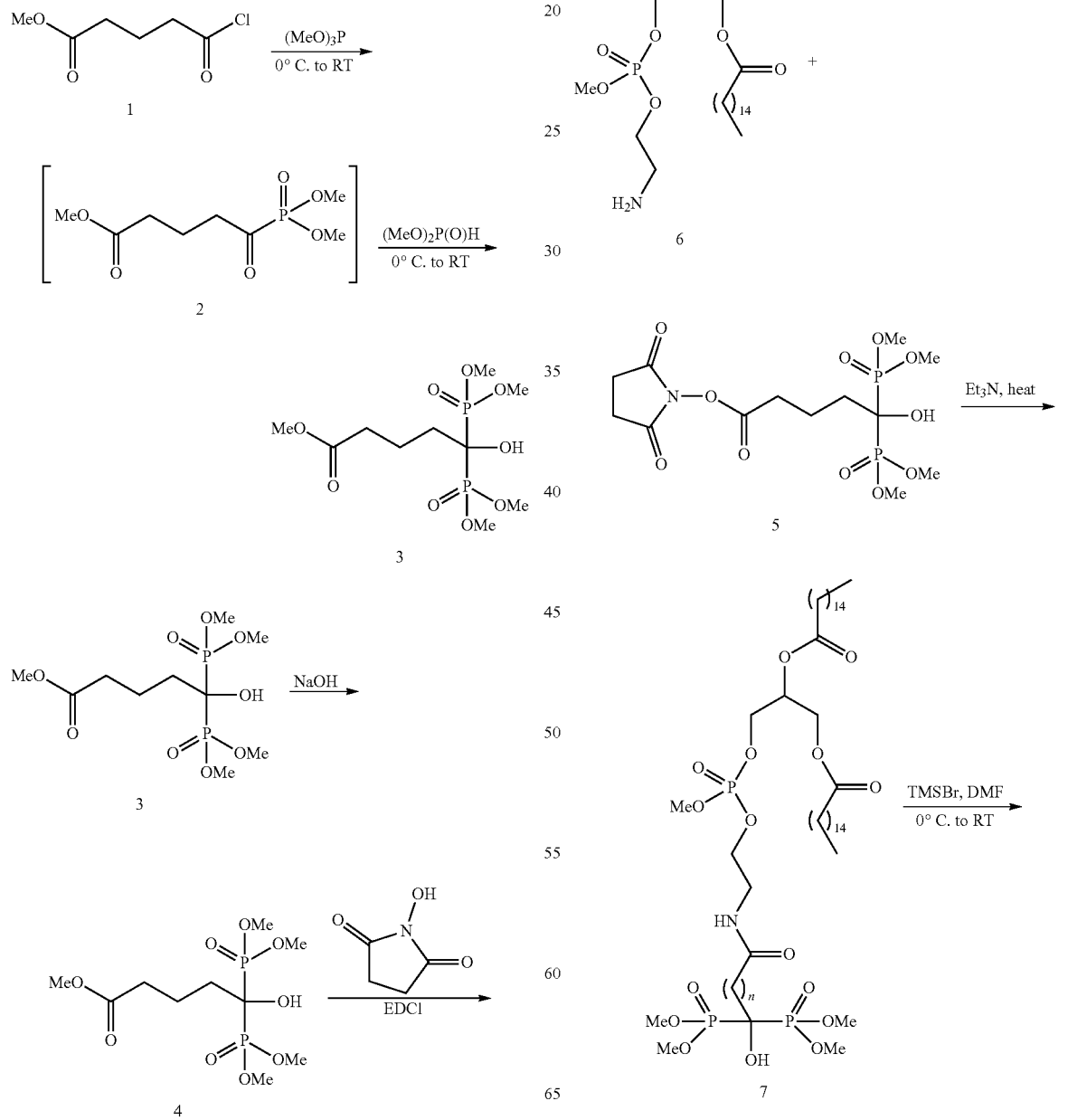

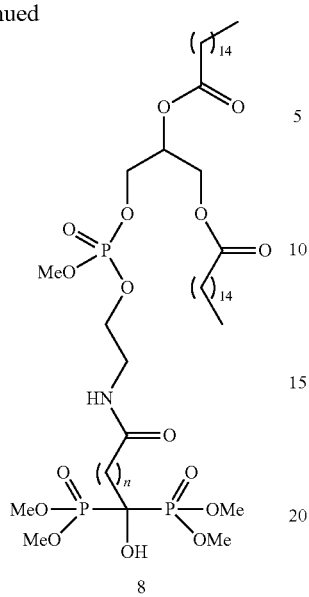

8

Example 2: Synthesis of Targeting Microbubbles

A solution of microbubbles (untagged) was synthesized according to the following procedure.

Material Source Information: For MPEG 5000 DPPE, the sodium salt was used rather than the ammonium salt. Source: Genzyme Pharmaceuticals. DPPA: 1,2-dipalmitoyl-sn-glycero-3-phosphate, monosodium salt. Source: Avanti Polar Lipids. DPPC: 1,2-dipalmitoyl-rac-glycero-3-phosphocholine hydrate, approx. 99%. Source: Sigma.

Combined Phospholipids 2.times. Stock Solution (in water): Prepared according to the following table.

| Lipids | Conc. In Definity | Mg in 50 mL of 2X stock soln. |
| --- | --- | --- |
| DPPA | 0.45 mg/mL | 4.5 mg |
| DPPC | 0.401 mg/mL | 40.1 mg |
| MPEG5000 DPPE | 0.304 mg/mL | 30.4 mg |

The lipids were dissolved in water by heating to between 60-80° C. The lipid solution was stored at 3° C. after preparation.

Buffer Solution: Prepared according to the following table.

| Material | Conc. in Definity | Conc. in 2X stock |
| --- | --- | --- |
| Propylene glycol | 103.5 mg/mL | 207.0 mg/mL |
| Glycerin | 26.2 mg/mL | 252.4 mg/mL |
| NaPhosphate monobasic x 1H2O | 2.34 mg/mL | 4.68 mg/mL |
| NaPhosphate dibasic, 10-hydrate | 2.16 mg/mL | 4.32 mg/mL |
| NaCl | 4.87 mg/mL | 9.74 mg/mL |
| Water to 50 mL | | |

The buffer solution was prepared at room temperature. 400 μL of lipid mix stock solution and 400 μL of buffer solution were transferred to amber vials, which were then sealed with silicone injection septum and screw cap. The vial headspace was flushed with octafluoropropane. As needed, the vial is shaken 30 seconds in VialMix shaker at reduced temperature.

Additional details for preparing Definity microbubbles (untagged) are found in the procedure reported in Unger et al., Adv. Drug Delivery Rev., 56 (2004) 1291-1314, and references cited therein.

Example 3: Synthesis of Targeting Microbubbles Via Cross-Metathesis

Olefin metathesis is extensively used to rearrange carbon-carbon double bonds in various organic syntheses. Especially, the second generation Grubbs catalysts, which are ruthenium atom centered and contain saturated mesityl-substituted N-heterocyclic carbene ligand, is suitable to prepare proposed microbubble chemical structures due to high catalytic efficiency together with high tolerance of diverse functional groups, organic solvents in the air. The chemical tag, bisphosphonate, can be introduced to the phospholipid, bubble-forming material, by two synthetic routes.

In the first method, the carbon double bond containing phospholipid, 5, and bisphosphonate containing structure, 2, are synthesized separately to produce product 2 and 5. Cross-metathesis can be performed between product 5 and product 2 in the presence of 2nd generation Grubbs catalyst. The cross-metathesis can prevent possible homodimerization of product 2 due to poor electron density of carbon double bond of 2. Therefore, this selective cross-metathesis will help to avoid additional purification step to separate desired product 6 and undesired byproduct, homodimerized products.

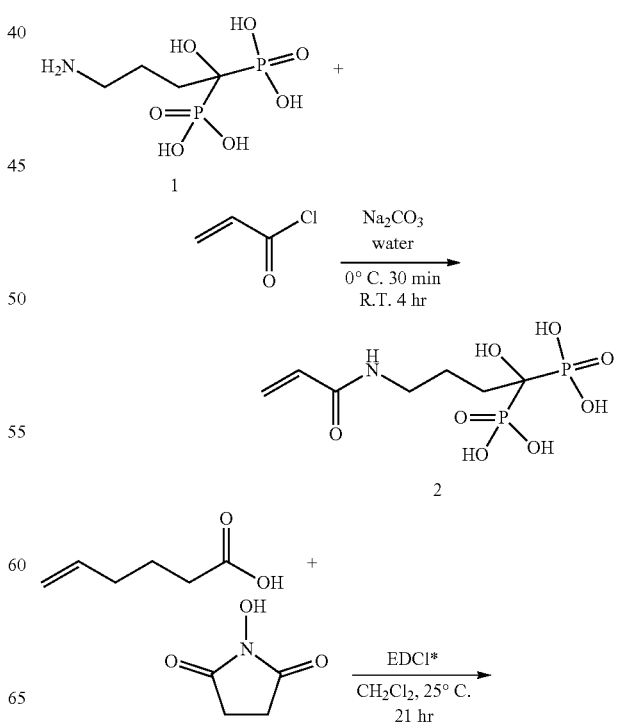

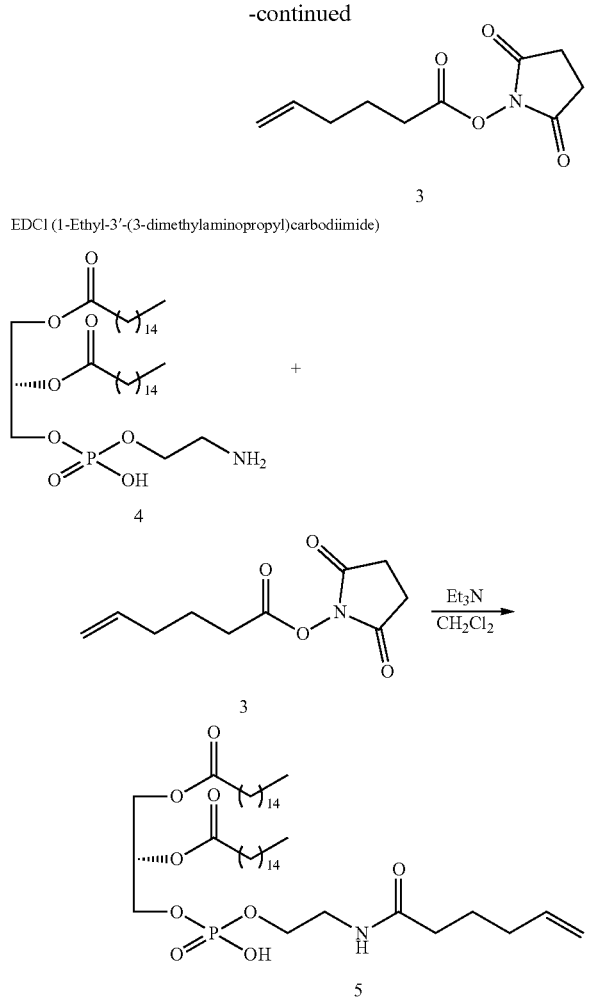
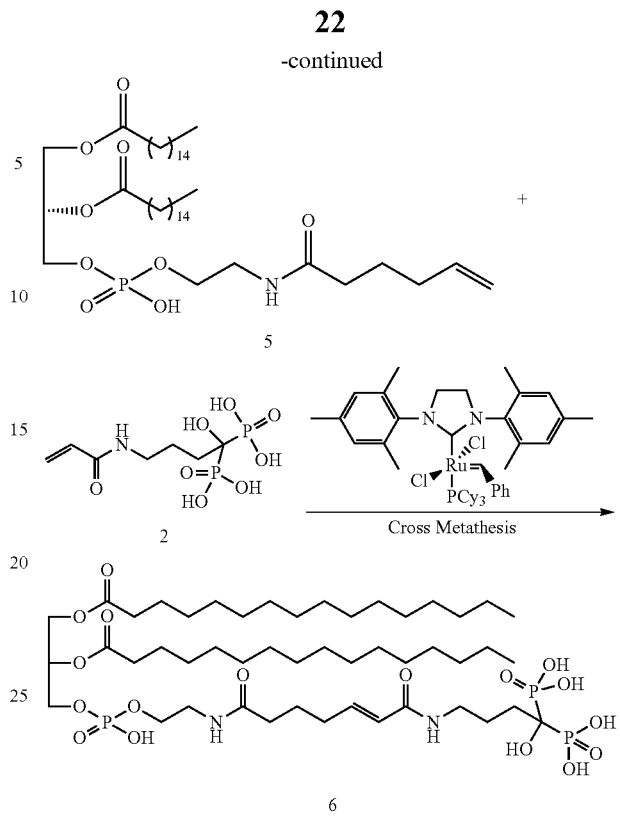

An alternative synthetic method to produce bisphosphonate containing phospholipid is shown in the following scheme. Unlike previous synthetic route, cross-metathesis reaction was carried out prior to introduction of bisphosphonate to phospholipids. Highly efficient reaction between NHS and primary amine can produce compound 8 without other undesired products.

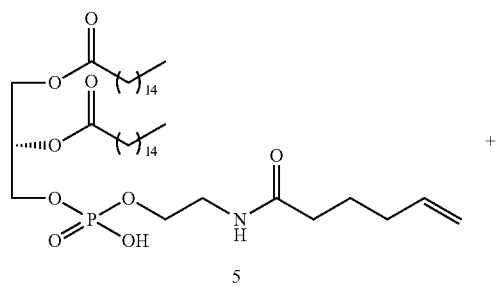

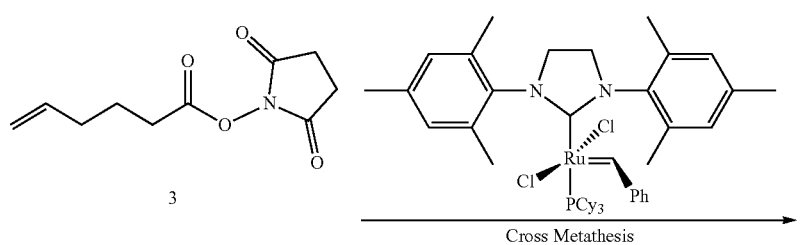

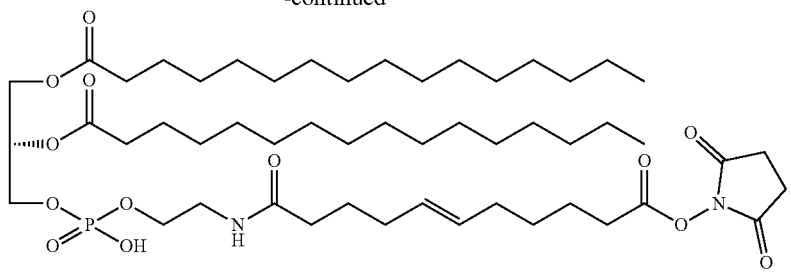

7

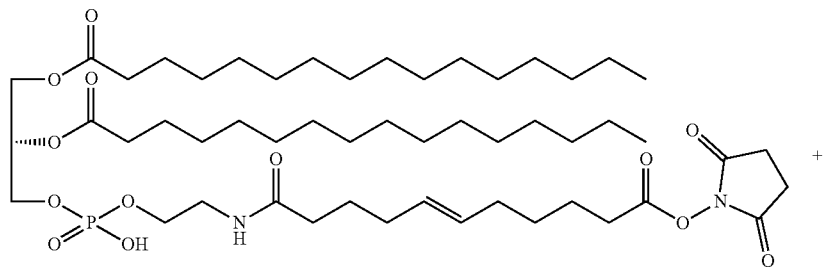

7

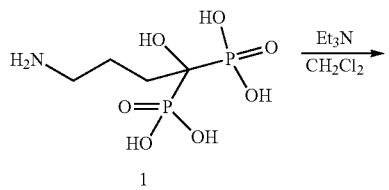

1

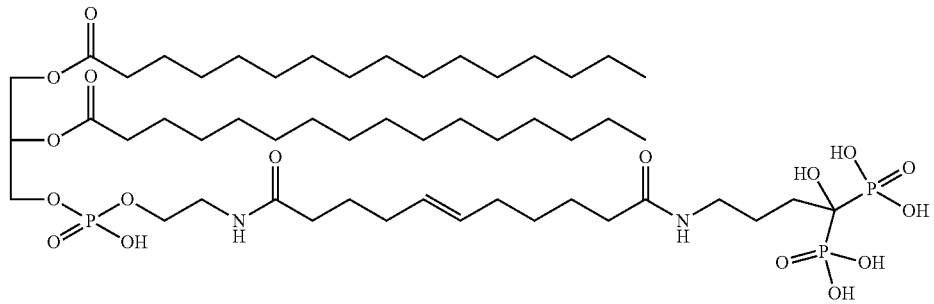

8

Example 4: In Vivo Administration of Microbubbles and Urinary Stone Fragmentation Rats (n=2) were anesthetized and a small intramuscular pocket was developed to instill 1.5-2.0 ml of microbubbles followed by placement of a single urinary stone composed of calcium phosphate and calcium oxalate (1.5 grams). This was repeated in a remote location with the same animal with a new stone fragment of the same composition. The intramuscular pockets were closed with 3.0 dexon sutures and the skin was closed with sub-cuticular sutures. A 7.5 mHz ultrasonic transducer was then applied to the skin with coupling gel. The stone and microbubbles were easily identified. Ultrasonic energy was applied for 15-20 minutes with direct visualization of both the stone and associated microbubbles. The stone was retrieved and post-procedure stone weight decreased by approximately 0.2 gram (dry then wet weight). Gross visualization revealed significant pitting on the stone surface demonstrating proof of concept of urinary stone fragmentation with microbubbles activated by ultrasonic energy. An image of the stone is provided in FIG. 1.

Figure 2:
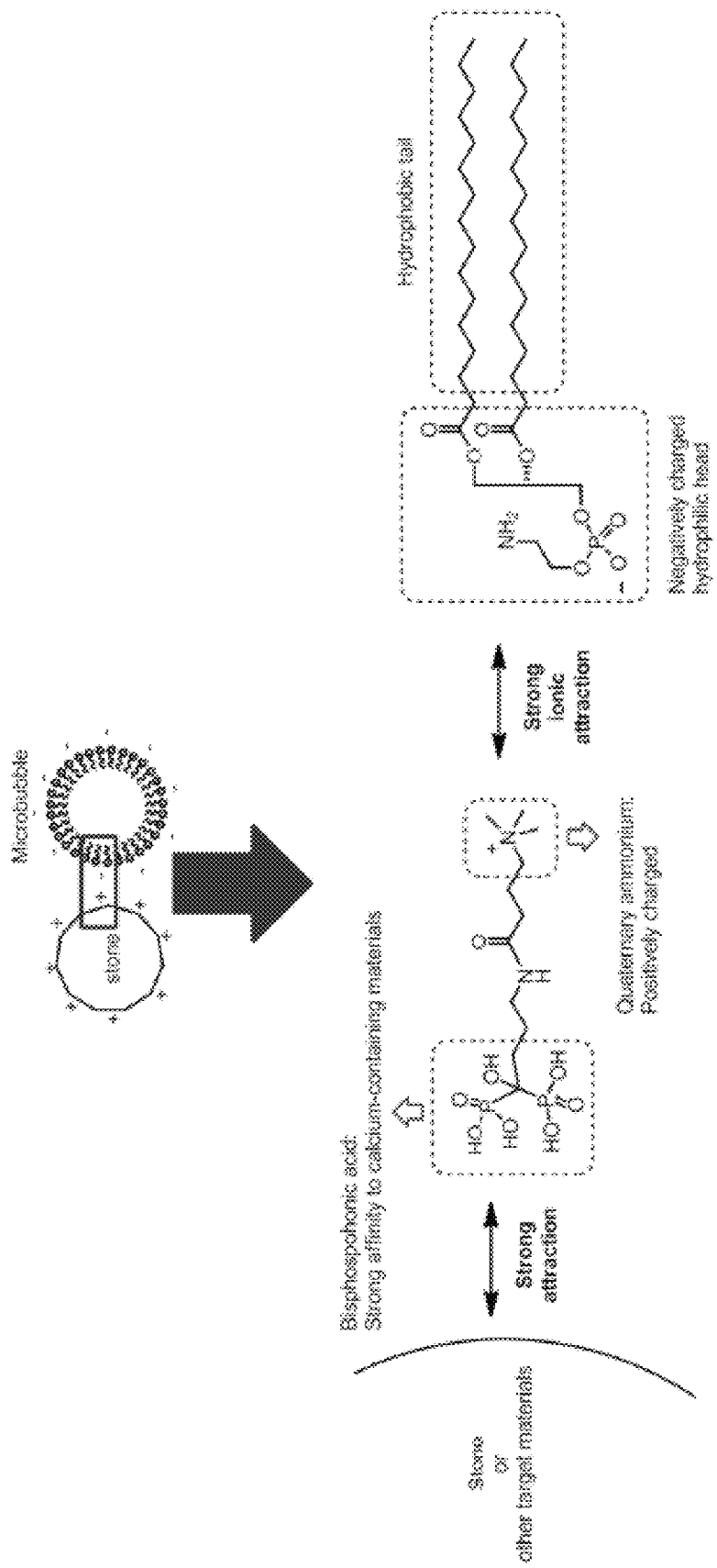
FIG. 2 illustrates one embodiment of the present invention in which a dipolar compound (bisphosphonic acid linked to a quaternary ammonium compound) serves to conjoin a target material with a negatively charged anchoring moiety (e.g., phospholipid) attachable to a microbubble.

Example 5: Attachment of Pendant Linker Groups to Attach Microbubbles to Calcium-Containing Materials A series of experiments were conducted using chemistry in which the anchoring moiety and the targeting moiety are linked via an ionic charge bond, demonstrating that microbubbles comprising, e.g., phosphonate coating structures can be appended to, e.g., calcium-containing materials (in this case, kidney stones) which have been modified to present a cationic surface (in this case, acid or quarternary ammonium salts) using the methods described herein. This principle is illustrated in FIG. 2.

Figure 3A:
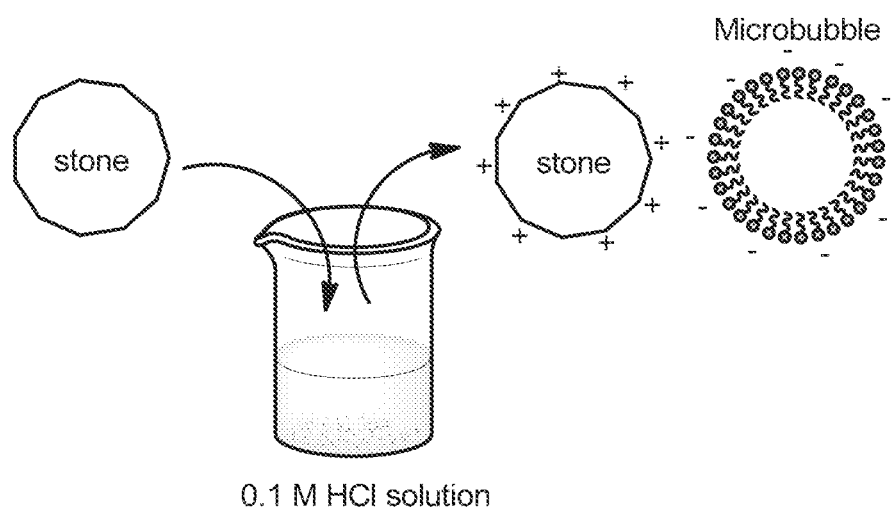
FIG. 3A provides a pictorial representation of treatment of a kidney stone with HCl.
Figure 4A:
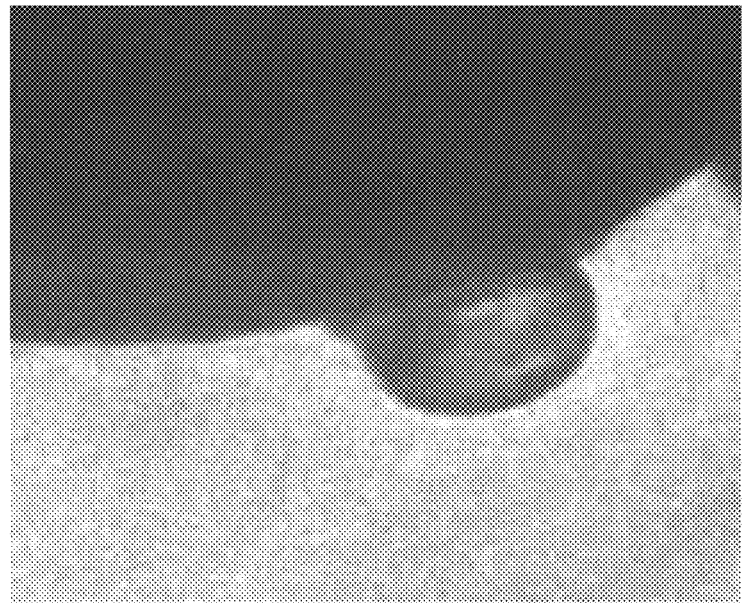
FIGS. 4A, 4B, and 4C show attachment and cavitation of microbubble to kidney stone, and damage caused thereby. See Example 5.
Figure 4B:
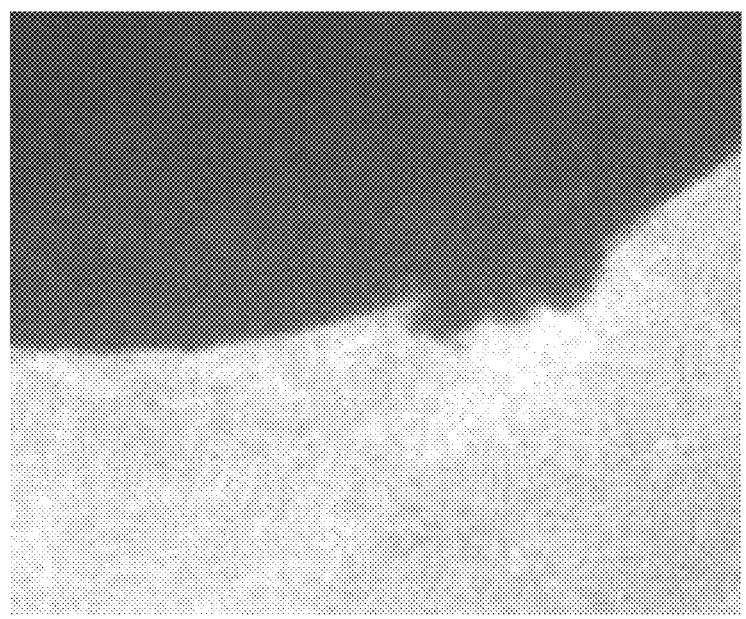
Figure 4C:
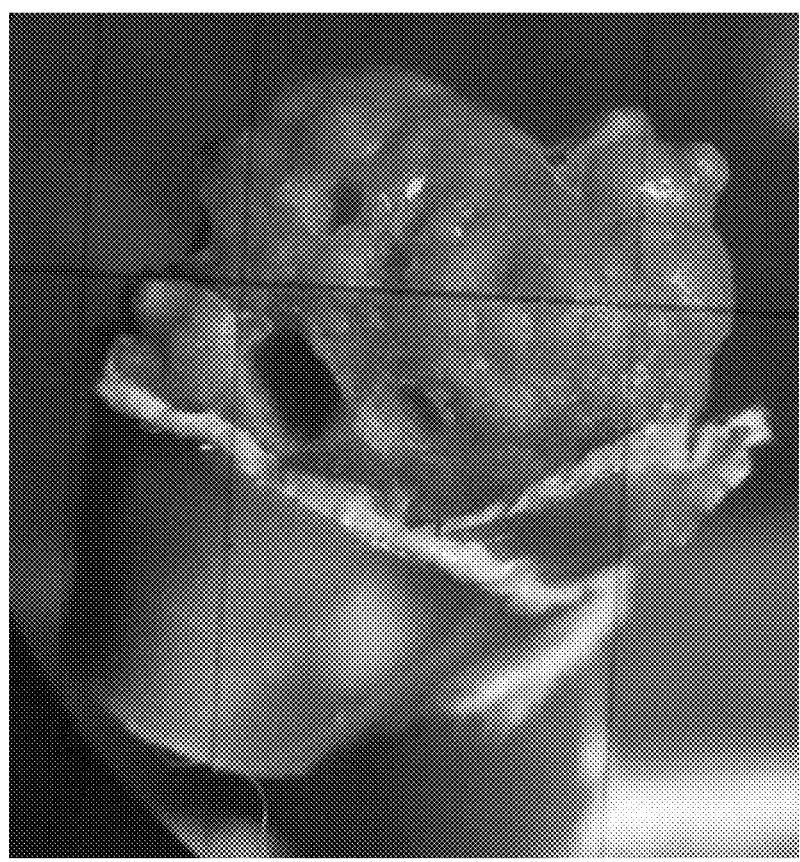

In one set of experiments, a kidney stone (calculous) was treated with 0.1 M HCl, as shown pictorially in FIG. 3A, thus generating a positive charge on the surface of the stone (calculous). When placed in the presence of microbubbles containing a negatively charged phospholipid coating (DEFINITY™ microbubbles), the microbubbles were shown to adhere to the positively charged stones (see, e.g., FIG. 4A). Upon application of ultrasonic energy, the microbubbles exhibited cavitation (FIG. 4B), after which the stones where shown to exhibit fracture damage (FIG. 4C).

Figure 3B:
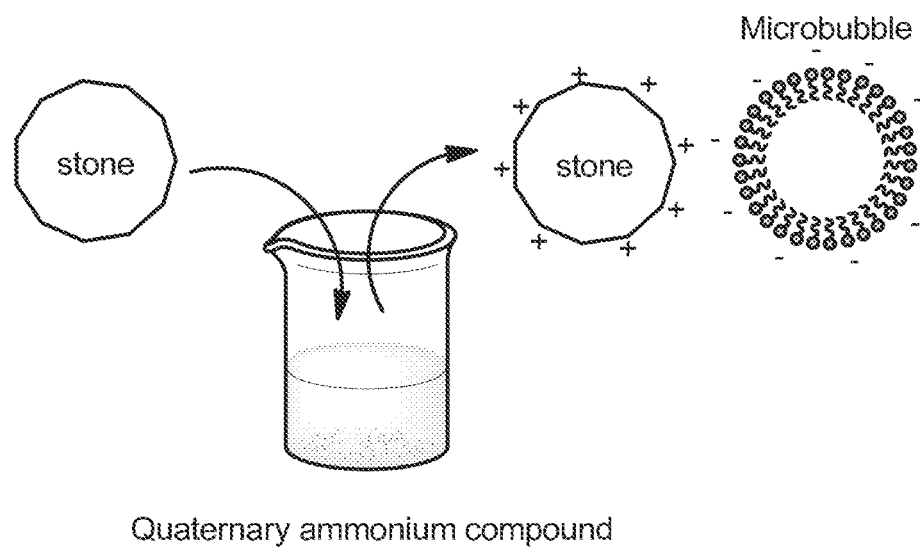
FIG. 3B provides a pictorial representation of treatment of a kidney stone with linked quaternary salt as described in Example 5.

A similar strategy may use targeting groups linked to cationic residues, thereby providing positively charged pendants attached to the metal-containing, especially calcium-containing materials which are attachable to microbubbles via ionic bonding to negatively charged microbubbles (e.g., pictorially shown in FIG. 3B).

One such synthetic scheme available, using the methods described herein, involves the preparation of a quaternary ammonium compound based on, for example, alendronic acid:

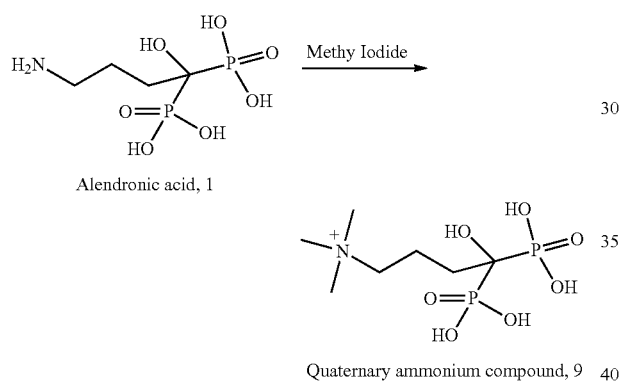

The bisphosphonate moiety (in this case, bisphophonic acid) has been shown to exhibit a sufficiently strong attraction to kidney stones to withstand cavitation and fracture of the stone.

Additional materials are available from related starting materials, using chemistries recognized by the skilled artisan:

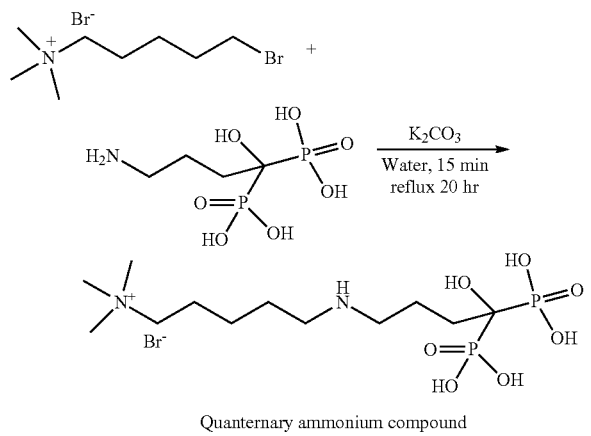

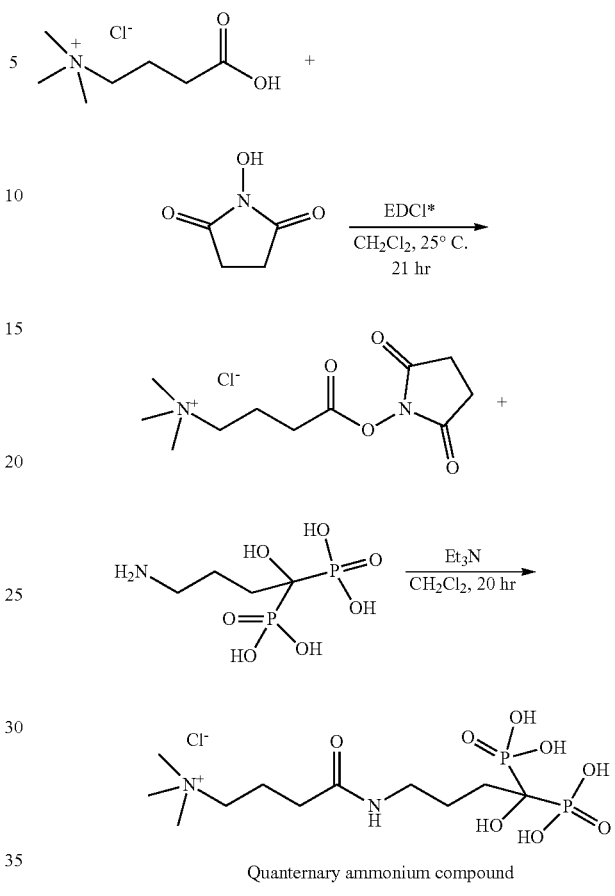

*EDCl (1-Ethyl-3'-(3-dimethylaminopropyl)carbodiimide)

Calcium-containing materials may be treated by such quaternary ammonium compounds either before microbubble injection or simultaneously with microbubble injection.

Example 6: Synthesis of Microbubbles Using Small Molecule Cancerous Tumor Cell Specific Ligands Microbubbles can also be prepared so as to target tumors using small molecule targeting moieties, including small molecule cancerous tumor cell specific ligands. Such microbubbles can optionally comprise therapeutic pharmaceutical agents, or can be used simply to direct ultrasonic energy to damage or break-up the calculous or tumor body. There are many examples of small molecule cell specific agents, though none of these appear to have been used as described in the present context. In this non-limiting example, folate—which is known to be a very selective receptor to cancerous tumor and it is not harmful to healthy cells.—is shown to be incorporated into a phospholipid moiety as the target of the microbubble structure. An exemplary synthetic scheme is shown below.

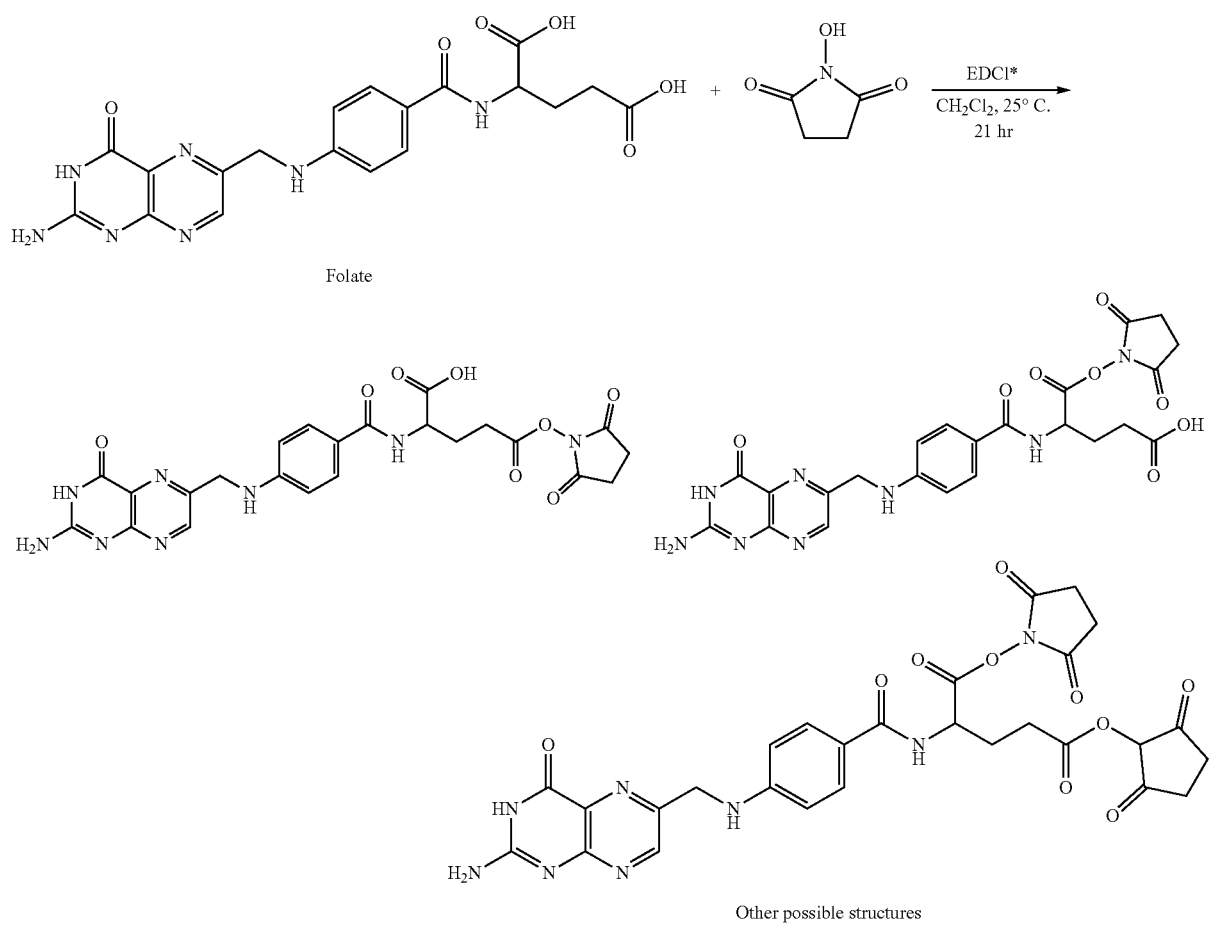

*EDCl (1-Ethyl-3'-(3-dimethylaminopropyl)carbodiimide)

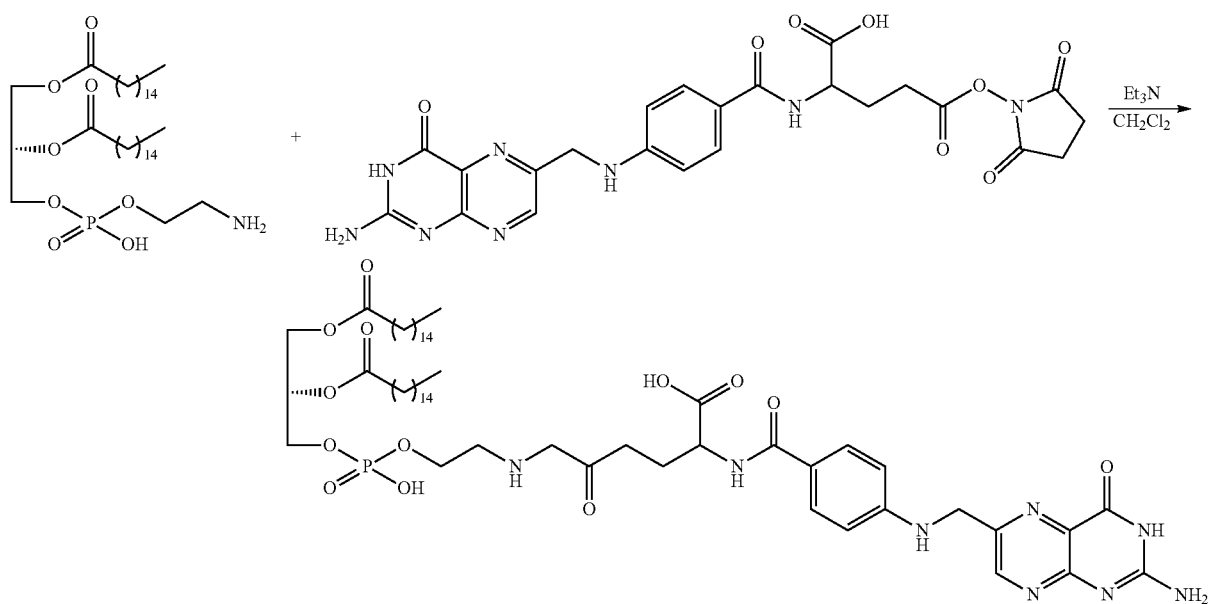

It should be appreciated that other small molecule targeting moieties may be similarly attached, by methods known by the skilled artisan, using the teachings described herein, and these are considered within the scope of the present invention.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A targeting microbubble comprising:
    (a) a core containing a fluid having a normal boiling point less than 30 C; and
    (b) a compound selected from the group consisting of:

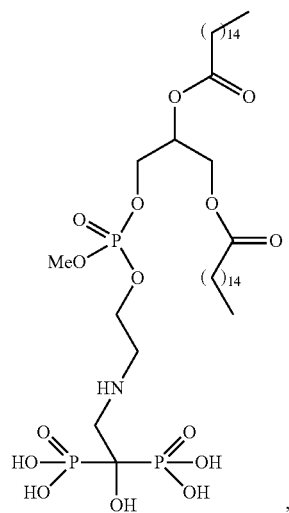

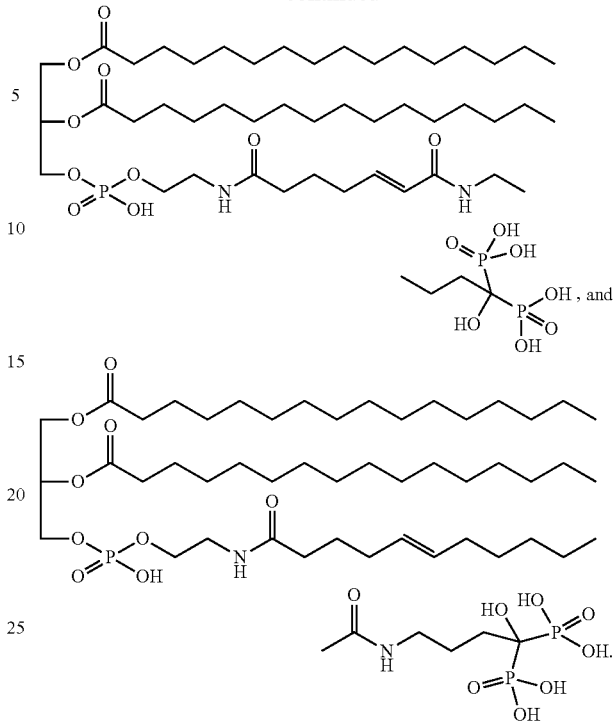

2. The targeting microbubble of claim 1, wherein the fluid is air, $CO_2$, a fluorinated or perfluorinated $C_{1-6}$ hydrocarbon, or a combination thereof.

3. The targeting microbubble of claim 1, wherein the fluid is a fluorinated hydrocarbon selected from perfluoropropane and perfluoropentane.

4. The targeting microbubble of claim 1, further comprising a polymeric linking moiety.

5. A solution comprising a plurality of the targeting microbubbles of claim 1 dispersed in a solvent.

6. The solution of claim 5, wherein the solvent is water or a physiological fluid.

7. The solution of claim 5, wherein the plurality of targeting microbubbles have an average diameter in the solution in the range of 1 micron to 10 microns.

* * * * *